United States Patent [19]

Iwase et al.

[11] Patent Number: 5,342,489
[45] Date of Patent: Aug. 30, 1994

[54] METHOD OF MEASURING OXYGEN ACTIVITIES IN SLAG

[75] Inventors: Masanori Iwase, Kyoto; Ryuji Fujiwara, Hirakata; Ryo Mochizuki, Osaka, all of Japan

[73] Assignee: Yamari Electronite Kabushikigaisha, Osaka, Japan

[21] Appl. No.: 690,892

[22] PCT Filed: Oct. 15, 1990

[86] PCT No.: PCT/JP90/01324

§ 371 Date: Jun. 17, 1991

§ 102(e) Date: Jun. 17, 1991

[87] PCT Pub. No.: WO91/06003

PCT Pub. Date: May 2, 1991

[30] Foreign Application Priority Data

Oct. 17, 1989 [JP] Japan .................................. 1-271033

[51] Int. Cl.$^5$ .......................................... G01N 27/417
[52] U.S. Cl. .................................... 204/153.18; 204/422
[58] Field of Search ................... 204/153.18, 421–429

[56] References Cited

U.S. PATENT DOCUMENTS

| | | |
|---|---|---|
| 3,281,137 | 10/1966 | Alper et al. ........................ 266/280 |
| 3,616,407 | 10/1971 | Engell et al. ...................... 204/423 |
| 3,652,427 | 3/1972 | Flood et al. .................... 204/153.18 |
| 3,661,725 | 5/1972 | Ulrich et al. ..................... 204/153.2 |
| 3,794,569 | 2/1974 | Kawai et al. ........................ 204/422 |
| 4,639,304 | 1/1987 | Bader et al. ........................ 204/422 |
| 5,096,165 | 3/1992 | Auer et al. ........................ 266/280 |

FOREIGN PATENT DOCUMENTS

| | | |
|---|---|---|
| 8513976 | 8/1985 | Fed. Rep. of Germany . |
| 3811865C1 | 5/1989 | Fed. Rep. of Germany . |
| 59-17148 | 1/1984 | Japan . |
| 59-103266 | 7/1984 | Japan . |
| 59-195559 | 12/1984 | Japan . |

*Primary Examiner*—T. Tung
*Attorney, Agent, or Firm*—Armstrong, Westerman, Hattori, McLeland & Naughton

[57] ABSTRACT

A method and apparatus for measuring the oxygen activity of the slag in molten iron or molten steel with high accuracy. A conventional measuring method in which an oxygen concentration cell produced by winding a platinum contact electrode around the outer surface of a solid electrolyte of one end closed tube type is disposed directly in the molten slag involves a fear of producing an error in measurement due to the difficulty in positioning in the fluid slag and the defective contact with the contact electrode caused by the densification by the heat of the slag. In the present invention, the oxygen activity in the slag is not directly measured but a specific metal between which and the slag an oxygen equilibrium is established when it comes into contact with the slag is charged in a container together with the slag. The oxygen activity of the specific metal is measured so as to indirectly measure the oxygen activity in the slag. The problems caused by the defective contact between the solid electrolyte and the contact electrolyte are thus solved, thereby enabling measurement of the oxygen activity in the slag with high accuracy.

8 Claims, 3 Drawing Sheets

METHOD OF MEASURING OXYGEN ACTIVITIES IN SLAG

TECHNICAL FIELD

The present invention relates to a method of measuring with high accuracy the oxygen activity of slag in molten iron or molten steel which is produced in the steel making process, a measuring apparatus used for the method and a disposable crucible used for the apparatus.

BACKGROUND ART

A method is conventionally known of measuring the oxygen activity of the slag in molten iron or molten steel by winding in a close contact state a platinum contact electrode around the outer surface of a solid electrolyte in the form of a tube having one end closed or by coating the outer surface thereof with a platinum contact electrode to prepare an oxygen concentration cell, embedding the oxygen concentration cell in the end of the probe, and disposing a probe directly in a molten slag layer which is existent in the upper layer of the molten steel in a converter or a ladle during operation.

Since the surface of the slag flows violently, however, it is difficult to exactly locate the oxygen concentration cell, which serves as a detecting portion, in the slag, so that the times at which measurement succeeds is low. Since the detecting portion is exposed to a high temperature for a long time, a firm heat-resistant material is necessary, therefore the probe becomes thick and heavy, and thus difficult to handle. In addition, it is necessary to bring the platinum into contact with the surface of the solid electrolyte in order to produce the oxygen concentration cell in the above-described form. Since the solid electrolyte is densified by the heat of the slag during operations, it is difficult to constantly maintain the contact state and thus a defective contact between the solid electrolyte and the contact electrode is produced, which results in the production of an error in measurement. Furthermore, although it is necessary to stop the progress of the steelmaking process for the measurement, it is actually impossible to stop the steelmaking process for a long time. It is therefore impossible to use a probe-type oxygen measuring apparatus in an industrial furnace.

Accordingly, it is an object of the present invention to solve these problems in the prior art and to provide a method of measuring the oxygen activity of slag which is capable of measuring the oxygen activity of a slag with high accuracy and to provide an oxygen activity measuring apparatus which is used for the method and which is very easy to handle.

DISCLOSURE OF THE INVENTION

The present inventor thought of measuring the oxygen activity of a slag not directly but indirectly, by selecting a specific metal between which metal and a slag an oxygen equilibrium is established when it comes into contact with the slag, accommodating the metal and the slag in the same container and measuring the oxygen activity of the metal. By materializing this idea, the necessity of the contact electrode being in close contact with the surface of the solid electrolyte is obviated and the problem caused by the defective contact between the solid electrolyte and the contact electrode is solved.

In a first aspect of the present invention, there is provided a method of measuring the oxygen activity in a slag comprising the steps of: dissolving a specific metal which is hardly alloyed with iron and hardly produces an oxide in an inert atmosphere and which has a larger specific gravity than the slag in a steel crucible; immersing a solid electrolyte of a tube type having one end closed with a reference electrode provided therewithin in the specific metal and bringing a contact electrode into contact with the specific metal so as to form an electric closed circuit between the reference electrode and the contact electrode through the specific metal; and measuring the oxygen activity of the specific metal.

In a second aspect of the present invention, the above-described measuring method is materialized and there is provided an apparatus for measuring the oxygen activity in a slag comprising: a steel crucible disposed in a smelting furnace which is filled with an inert gas and accommodation the specific metal and the slag therein; and a solid electrolyte provided with a reference electrode therewithin and immersed in the slag; wherein the electromotive force between the steel crucible and the reference electrode is measured with the steel crucible as the contact electrode.

As the smelting furnaces for dissolving the slag and the specific metal in the steel crucible, it is possible to use a resistance furnace or a high frequency induction furnace, but a condensing radiation furnace is preferred from the point of view of high-speed heating.

As methods of holding the steel crucible, it is possible to place the steel crucible on a pedestal or to vertically and slidably hang the steel crucible. In the former case, it is also possible to use a conductive pedestal so that the pedestal also serves as a lead wire from the steel crucible. In the latter case, it is also possible to use a removable metal hanger so that the metal hanger also serves as a lead wire from the steel crucible.

It is possible to dissolve and solidify the specific metal on the inner surface of the steel crucible in advance and replace the steel crucible for each measurement instead of inserting the specific metal in the steel crucible at the time of measurement.

The oxygen activity in a slag is measured in the following manner by using the apparatus of the present invention.

A metal which is not alloyed with iron and hardly produces an oxide in an inert atmosphere, namely, the specific metal, is accommodated in the steel crucible in a solidified state and a slag being measured is charged into the steel crucible.

The steel crucible is then accommodated in a furnace which is filled with an inert gas and heated so as to melt the slag and the specific metal.

A solid electrolyte of a tube type with one end closed with a reference electrode provided therewithin is then passed through the slag layer in the molten state so as to be immersed in the specific metal. By inferring the oxygen activity in the specific metal, the oxygen activity in the slag is measured.

Since the specific metal is not alloyed with iron and does not produce an oxide, an oxygen equilibrium is established between the slag and the specific metal and the oxygen activity in the specific metal has a correlation with the oxygen activity in the slag. It is therefore possible to measure the oxygen activity in the slag from the oxygen activity in the specific metal. In addition, since the specific metal has a conductivity unlike the slag which is an insulator, an electric closed circuit is formed between the reference electrode and the contact electrode, so that it is possible to obtain the oxygen activity in the specific metal by measuring the electromotive force between the reference electrode and the steel crucible.

In the case of using a condensing radiation furnace as the heat source for the smelting furnace, high-speed melting is possible, thereby greatly shortening the time required for the measurement of the oxygen activity. In the case of vertically and slidably hanging of the steel crucible as a method of holding the steel crucible, it is possible to set and take out the steel crucible together with the solid electrolyte from above. In the case of using a conductive metal hanger or a pedestal which is provided separately from the steel crucible, since these members can also function as a lead wire from the steel crucible, it is unnecessary to provide a connecting terminal for leading the electromotive force on the steel crucible.

If a disposable crucible is provided by dissolving and solidifying the specific metal on the inner surface of the steel crucible in advance, the problem of inserting the specific metal in the steel crucible for each measurement is avoided, and since the steel crucible once used is discarded, there is no slag remaining in the steel crucible as in the case of repetitive use, thereby enabling measurement with high accuracy.

BEST MODE FOR CARRYING OUT THE INVENTION

Figure 1:
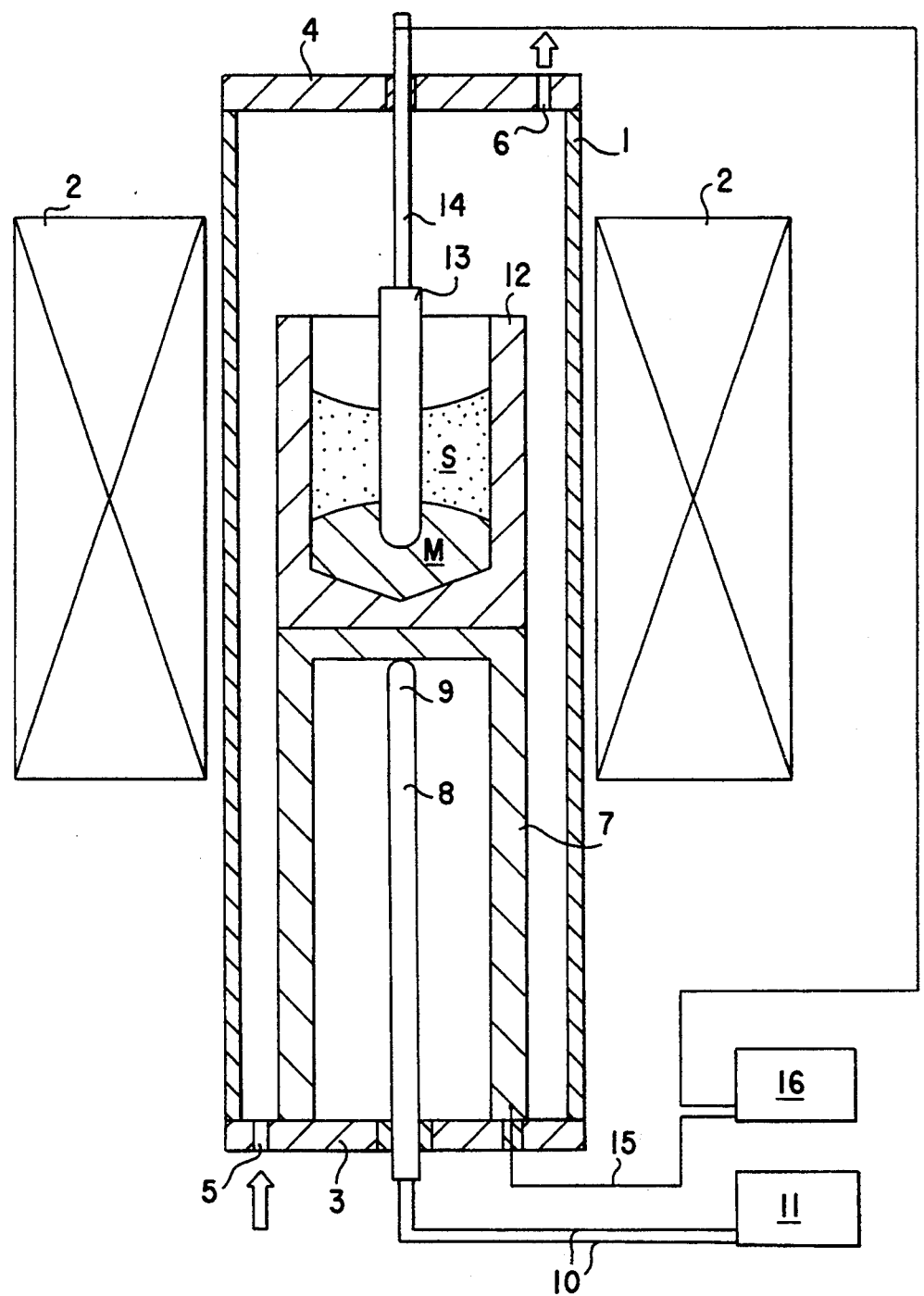
FIG. 1 is a schematic explanatory sectional view of an embodiment of an apparatus for measuring the oxygen activity in a slag according to the present invention.

The details of the present invention will now be explained with reference to the illustrated embodiments. FIG. 1 is a schematic explanatory sectional view of the structure of an oxygen activity measuring apparatus according to the present invention. In FIG. 1, the reference numeral 1 represents a reaction tube composed of a heat-resistant material such as alumina, mullite and quartz. The reaction tube 1 is situated at the center of a furnace body 2, which is the heat source in a smelting furnace. As the smelting furnace, it is possible to use a condensing radiation furnace, a high frequency induction furnace or a resistance furnace. A condensing radiation furnace is especially preferred. A condensing radiation furnace is advantageous in that since the temperature control is easy, the time required for raising the temperature is short and strong heating is possible, it is possible to melt a slag in a short time.

The reaction tube 1 is hermetically sealed in the vertical direction by a bottom plate 3 and a cover 4, and the bottom plate 3 is provided with a gas inlet 5 for introducing an inert gas such as nitrogen gas and argon gas to the interior of the reaction tube 1, while the cover 4 is provided with a gas outlet 6 for discharging the inert gas from the interior of the reaction tube 1.

The reference numeral 7 represents a pedestal for placing the steel crucible thereon, and a temperature element 8 is disposed in the pedestal 7 with a temperature sensing portion 9 in contact with the upper end surface of the inner surface of the pedestal 7. The lower end of the temperature element 8 is led out of the reaction tube 1 through the bottom plate 3, and lead wires 10 led out of the temperature element 8 are connected to a temperature measuring instrument 11.

The reference numeral 12 represents a steel crucible placed on the pedestal 7 in contact therewith. The steel crucible 12 accommodates a slag S, which is the object of measurement, and a specific metal M. As the specific metal M, any metal may be adopted that is not alloyed with iron, hardly produces an oxide and that has a larger specific gravity than the slag S. For example, silver and copper are usable. In this embodiment, silver is used.

The slag S and the specific metal M are melted by the heat of a smelting furnace, and a one end closed tube type solid electrolyte 13 with a reference electrode (not shown) provided therein is immersed in the molten specific metal M. A lead 14 on the reference electrode side which is led from the solid electrolyte 13 is introduced to the outside of the reaction tube 1 through the cover 4 of the reaction tube 1. On the other hand, a lead wire 15 is led out of the pedestal 7 which is electrically conductive with the steel crucible 12 through the bottom plate 3, thereby constituting a lead on the contact electrode side. Thus, an oxygen concentration cell is formed between the lead on the reference electrode side and the lead on the contact electrode side. A measuring instrument 16 for measuring the electromotive force produced by the oxygen concentration cell is provided between the lead on the reference electrode side and the lead on the contact electrode side.

Figure 2:
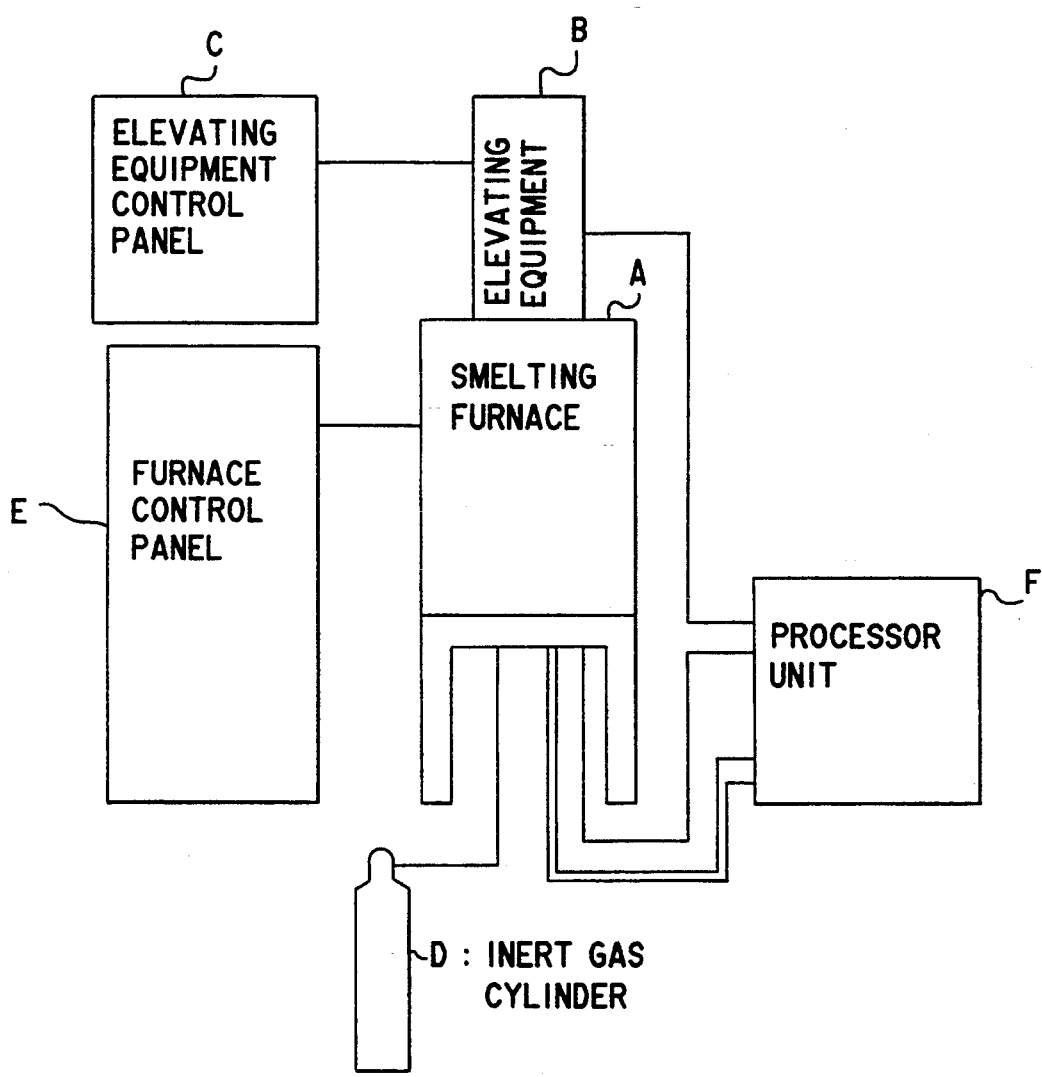
FIG. 2 is an explanatory view of the structure of the embodiment shown in FIG. 1 and peripheral devices.

The oxygen activity measuring apparatus having the above-described structure is used after peripheral devices are arranged therearound so as to constitute a complete measuring apparatus, as shown in FIG. 2. The symbol A represents a smelting furnace which accommodates the reaction tube 1 and the furnace body 2, and an elevating equipment B for elevating the solid electrolyte 13 is disposed above the smelting furnace A. The symbol C represents an elevating equipment control panel for controlling the elevating equipment B. An inert gas is supplied to the reaction tube 1 disposed in the smelting furnace A by using a inert gas cylinder D disposed outside of the smelting furnace, and the environment in the furnace including the furnace temperature is controlled by a furnace control panel E. The temperature obtained from the temperature element 8 and the electromotive force produced by the oxygen concentration cell are input to a processor unit F having the measuring instruments therein and processed.

The oxygen activity measuring apparatus having the above-described structure is used in the following manner.

The slag S and the specific metal M which are collected from a converter and a ladle are first charged into the steel crucible 12. At this time, although the specific metal M is in a solidified state, the slag S may be either in the solidified state or in the molten state. It goes without saying, however, that use of the slag S in the molten state is preferred from the point of view of shortening the measuring time.

The steel crucible 12 is then accommodated in the reaction tube 1 by removing the bottom plate 3 to take out the pedestal 7, placing the steel crucible 12 on the pedestal 7 in contact therewith, and inserting the pedestal 7 with the steel crucible 12 placed thereon into the reaction tube 1 from below. When the steel crucible 12 is disposed in the reaction tube 1 in this way, an inert gas flows from the gas inlet 5 to fill the reaction tube 1 with the inert gas, and the smelting furnace A is then operated to rapidly heat the interior of the reaction tube for the purpose of melting the slag S and the specific metal M. The specific metal is preferably rapidly heated. Especially, by using a condensing radiation furnace as the smelting furnace A, it is possible to rapidly raise the temperature and, in addition, a fear of producing noise which influences the instruments is precluded unlike a high frequency induction furnace.

After the slag S and the specific metal M have been made molten, the solid electrolyte 13 is lowered from above the steel crucible 12 and passed through the slag layer, and the end portion of the solid electrolyte 13 is immersed in the specific metal M. In this state, an oxygen concentration cell is formed between the reference electrode and the steel crucible, which is the contact electrode, with the solid electrolyte 13 and the special metal M therebetween, and the electromotive force produced by the oxygen concentration cell is measured by the instrument 16 which is connected between the lead on the reference electrode side and the lead on the contact electrode side. The temperatures of the slag S and the specific metal M are constantly measured by the temperature element 8 provided in the pedestal 7 and indicated to the temperature measuring instrument 11. By processing these values, the oxygen activity of the specific metal is calculated. Since a metal which is not alloyed with iron and hardly produces an oxide is used as the special metal M, an oxygen equilibrium is established between the specific metal M and the slag S and a correlation holds between both oxygen activities. It is thus possible to obtain the oxygen activity in the slag S on the basis of the oxygen activity in the specific metal M.

When the measurement of the oxygen activity is completed, the inert gas in the reaction tube 1 is discharged from the gas outlet 6. Thereafter, the steel crucible 12 is taken out from below the reaction tube 1, thereby completing the measurement process. When a condensing radiation furnace is used as the smelting furnace A, since it is possible to raise the temperature in a short time, the time required until the steel crucible 12 is taken out since it is accommodated in the reaction tube 1 is about 1 to 15 minutes. In this way, measurement of the oxygen activity is enabled very quickly.

In order to maintain the measuring accuracy of this apparatus, it is necessary to regularly calibrate the apparatus by inserting a standard in place of the slag. As the standard, a pure ferrous oxide or a mixture of ferrous oxide with a halide of alkaline earth metals and/or a halide of alkaline metals is used in this embodiment. It is naturally possible to use another standard so long as it has a constant oxygen activity.

Figures 3A, 3B:
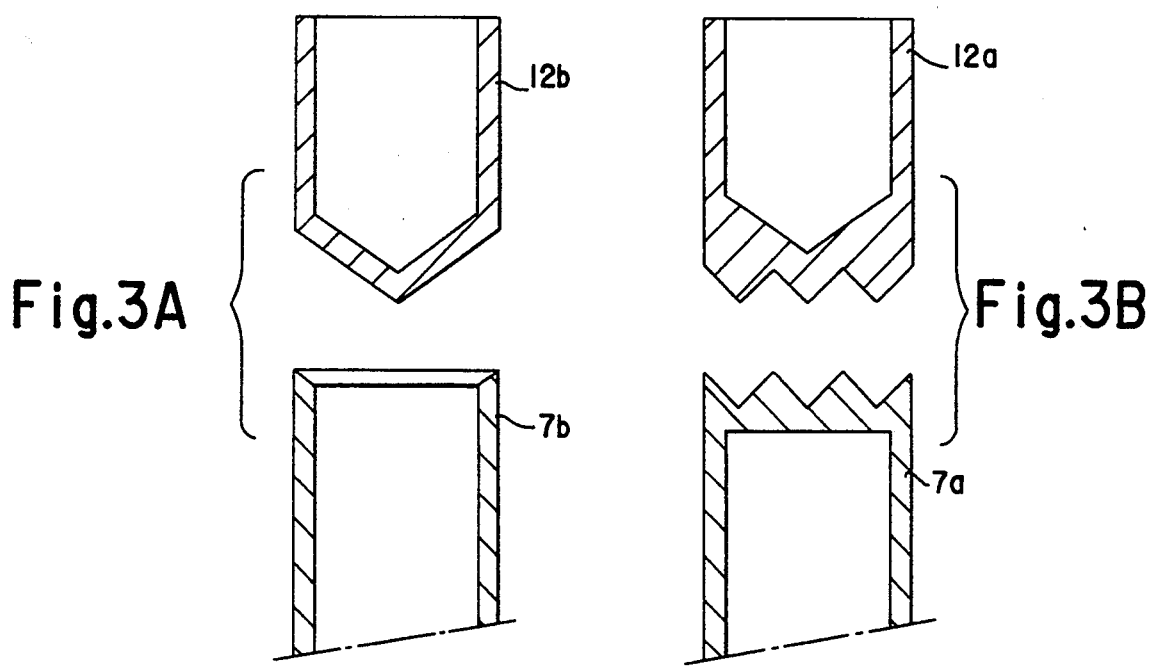
FIGS. 3A and 3B are explanatory views of other examples of the steel crucible and the pedestal.

The steel crucible 12 and the pedestal 7 shown in FIG. 1 have a structure in which the steel crucible 12 comes into contact with a flat mounting surface of the pedestal 7, but the steel crucible 12 and the pedestal 7 may have different configurations. For example, it is also preferable that the bottom surface of a steel crucible 12a and the mounting surface of a pedestal 7a undulate, as shown in FIG. 3B, thereby ensuring holding of the steel crucible 12 and electric contact therebetween. It is also possible to combine a steel crucible 12b having a tapered under surface and a cylindrical pedestal 7b having a tapered upper edge, as shown in FIG. 3A.

Figure 4:
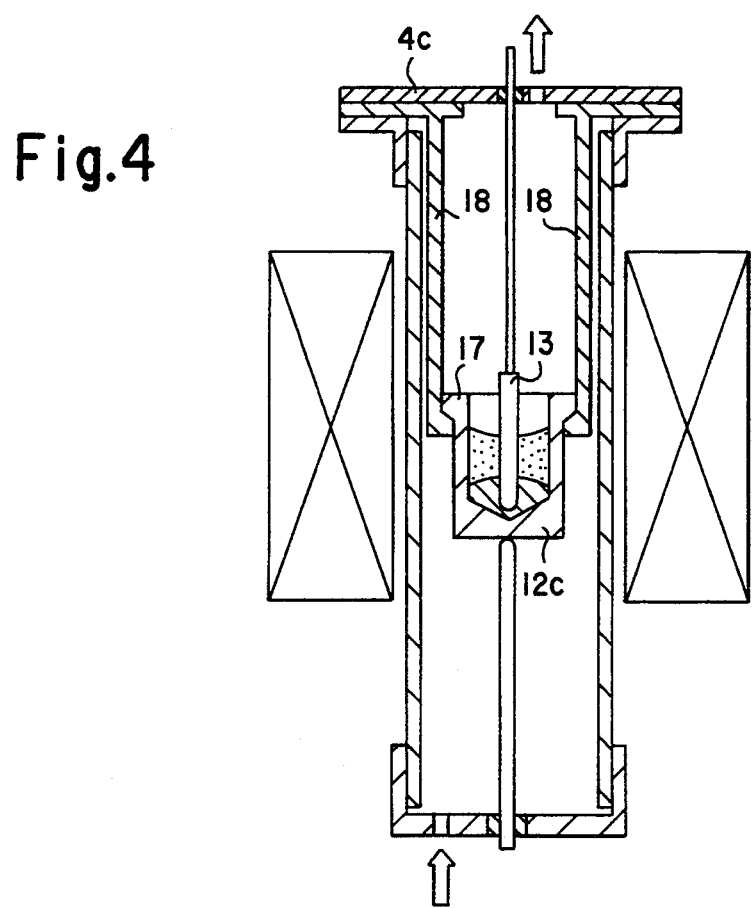
FIG. 4 is another embodiment of an apparatus according to the present invention which adopts a steel crucible hanging system.

FIG. 4 shows another embodiment in which a steel crucible 12c is hung and the pedestal is dispensed with. A retaining flange 17 is formed on the outer periphery of the opening of the steel crucible 12c, and the steel crucible 12c is hung by a plurality of metal hangers 18 which are hung down from a cover 4c in the form of arms. The steel crucible 12c and the metal hangers 18 have a different engaging structure and the configurations of the steel crucible 12c and the metal hangers 18 are appropriately selected in accordance with the engaging structure. If such a steel crucible hanging system is adopted, since the steel crucible 12c and the solid electrolyte 13 can be taken out of the reaction tube 1 merely by elevating the cover 4c, the trouble of taking out the steel crucible from below the reaction tube 1 and taking out the solid electrolyte from above the reaction tube 1 is omitted, thereby greatly simplifying the take-out operation and setting operation.

As another example of a steel crucible, it is possible to produce a disposable type steel crucible by melting and solidifying a specific metal such as silver on the inner surface of the steel crucible, and use a new disposable type steel crucible for each measurement. In this way, not only is the time for charging the specific metal in the steel crucible for each measurement saved but also since no slag other than the slag which is the object of measurement, for example, the slag subjected to the precedent measurement, remains in the steel crucible, measurement of oxygen activity with higher accuracy is enabled.

INDUSTRIAL APPLICABILITY

As described above, according to the method and apparatus for measuring the oxygen activity in a slag of the present invention, a specific metal between which metal and a slag which is the object of measurement, an oxygen equilibrium is established is selected and the specific metal is charged in a steel crucible together with the slag so as to measure the oxygen activity in the slag by measuring the oxygen activity in the specific metal. It is thus possible to measure the oxygen activity in the slag by measuring the electromotive force produced by the oxygen concentration cell formed between the lead on the reference electrode side and the lead on the contact electrode side through the specific metal. Since the solid electrolyte is situated in the specific metal in an immersed state, the contact between the specific metal and the solid electrolyte is complete. In addition, since the steel crucible is used as the contact electrode, the contact between the specific metal and the contact electrode can be made complete, thereby enabling measurement with high accuracy.

In the case of using a condensing radiation furnace as the smelting furnace, since high-speed heating is easy and temperature control is also easy, it is possible to greatly shorten the measuring time and, in addition, noise which influences the instruments is not produced unlike a high frequency induction furnace.

In the case of adopting a steel crucible hanging system, it is possible to take out both the steel crucible and solid electrolyte from above the reaction tube, thereby greatly facilitating the setting operation and take-up operation.

Furthermore, in the case of adopting a steel crucible hanging system, the hanging metal can serve as the lead on the contact electrode side, and in the case of adopting a system of placing the steel crucible on the pedestal, the pedestal can serve as the lead on the contact electrode side. In either case, the structure of the apparatus can be simplified without the need for providing a lead wire separately.

In the case of producing a disposable type steel crucible by melting and solidifying the specific metal in the steel crucible in advance, it is unnecessary to charge the specific metal for each measurement. It is possible to save the trouble of inserting the specific metal or to prevent the specific metal from being left in the steel crucible after measurement. In addition, since a new steel crucible is used for each measurement, it is possible to prevent a slag other than the slag which is the object of measurement from mixing therewith.

What is claimed is:

1. A method of measuring the oxygen activity of a slag from molten iron or steel, the method comprising the steps of: melting in an inert atmosphere a specific metal which does not alloy with iron, does not produce an oxide and which has a larger specific gravity than the slag which is being measured for oxygen activity, the metal being selected from the group consisting of copper and silver, together with said slag in a steel crucible; immersing a solid electrolyte in the form of a tube having a closed end and having a reference electrode provided therewith in said specific metal and bringing a contact electrode into contact with said specific metal so as to form an electric closed circuit between said reference electrode and said contact electrode through said specific metal; and measuring the oxygen activity of said specific metal from measured values from said electric closed circuit, and correlating the oxygen activity of the specific metal to the oxygen activity of the slag.

2. A method for measuring the oxygen activity of a slag according to claim 1, wherein said melting is conducted in a smelting furnace.

3. A method for measuring the oxygen activity of a slag according to claim 2, wherein said melting is conducted in a condensing radiation furnace.

4. A method for measuring the oxygen activity of a slag according to claim 2, wherein said steel crucible and said solid electrolyte are vertically and slidably hung down in said smelting furnace.

5. A method for measuring the oxygen activity of a slag according to claim 4, further comprising a metal hanger for removably hanging said steel crucible, said metal hanger also serving as a lead wire from said steel crucible which also serves as said contact electrode.

6. A method for measuring the oxygen activity of a slag according to claim 1, wherein said contact electrode is electrically connected to a conductive pedestal provided below said steel crucible, said pedestal serving as a lead wire from said steel crucible.

7. A method for measuring the oxygen activity of a slag according to claim 1, wherein said specific metal is silver.

8. A method for measuring the oxygen activity of a slag according to claim 1, wherein said specific metal is copper.

* * * * *